United States Patent
Uchida et al.

(10) Patent No.: US 7,167,735 B2
(45) Date of Patent: Jan. 23, 2007

(54) CONCENTRATION MEASURING INSTRUMENT, AND METHOD OF MEASURING THE CONCENTRATION OF A SPECIFIC COMPONENT IN A SUBJECT OF MEASUREMENT

(75) Inventors: Shinji Uchida, Osaka (JP); Kiyoko Ooshima, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 385 days.

(21) Appl. No.: 10/480,036

(22) PCT Filed: Mar. 18, 2003

(86) PCT No.: PCT/JP03/03187

§ 371 (c)(1),
(2), (4) Date: Aug. 12, 2004

(87) PCT Pub. No.: WO03/078981

PCT Pub. Date: Sep. 25, 2003

(65) Prior Publication Data
US 2004/0256563 A1      Dec. 23, 2004

(30) Foreign Application Priority Data
Mar. 19, 2002    (JP)   .............................. 2002-075732

(51) Int. Cl.
*A61B 5/00*    (2006.01)
(52) U.S. Cl. ........................ 600/310; 600/316; 600/322
(58) Field of Classification Search ................ 600/310, 600/316, 322, 336; 356/445; 422/82.05, 422/82.09, 82.11
See application file for complete search history.

(56) References Cited

U.S. PATENT DOCUMENTS
6,362,144 B1 *  3/2002  Berman et al. ............. 510/140
(Continued)

FOREIGN PATENT DOCUMENTS
JP       09-113439       5/1997
(Continued)

OTHER PUBLICATIONS
Japanese International Search Report for PCT/JP03/03187, dated Jul. 8, 2003.
(Continued)

Primary Examiner—Eric F. Winakur
Assistant Examiner—Jack Lin
(74) Attorney, Agent, or Firm—RatnerPrestia

(57) ABSTRACT

To provide a measuring method which enables a highly accurate measurement of concentrations of specific components in subjects of measurement even when the concentration measuring contact of a concentration measuring instrument is contaminated with drinks or the like.

The concentration measuring instrument includes:

a main body that has a concentration measuring contact, a light source and a photodetector; and judging means that calculates the difference between a non-contact-measured value, a value, measured by the photodetector while keeping a subject of measurement out of contact with the concentration measuring contact, of the quantity of light that is emitted and entered by the light source into the concentration measuring contact and returned to the concentration measuring contact and a predetermined reference value obtained in advance by making measurement while keeping the concentration measuring contact clean and judges whether the calculation of the concentration of the specific component in the subject of measurement is effective or not by comparing the calculated difference with a predetermined threshold.

20 Claims, 6 Drawing Sheets

U.S. PATENT DOCUMENTS

2003/0023152 A1* 1/2003 Abbink et al. .............. 600/316

FOREIGN PATENT DOCUMENTS

JP          09-325113 A    12/1997
WO     WO 03/021239 A1    3/2003

OTHER PUBLICATIONS

D. Bach et al., "Attenuated total reflection (ATR) Fourier transform infrared spectroscopy of dimyristoyl phosphatidylserine-cholesterol mixtures", Biochimica et Biophysica Acta, vol. 1514, No. 2, (2001), pp. 318-326.

M. Larsson et al., "Structure and Orientation of Collectors Adsorbed at the ZnS/Water Interface", Journal of Colloid and Interface Science, vol. 242, No. 1, (2001), pp. 25-30.

B. Jordanov et al., "An ATR Method for Measurement of IR Circular Dichroic Spectra", Journal of Molecular Structure, vol. 141 (Mar. 1986) pp. 297-300.

H. Fukushima et al., "Diabetes and BME, Noninvasive Blood Glucose Measurement, Development of Optical Glucose Sensor", BME, vol. 5, No. 8, (Japan ME Society, 1991).

Chinese Official Action for 03800816.5, dated Mar. 18, 2005 (with partial English translation).

Wang Dongan et al., "Quantitative Characterization of Absorbed Bovine Serum Album in on Modified Surfaces of Poly(ether urethane) Materials Using ATR-FT-IR Spectroscopy," Journal of Biomedical Engineering, vol. 19 (2002), pp. 4-9.

* cited by examiner

CONCENTRATION MEASURING INSTRUMENT, AND METHOD OF MEASURING THE CONCENTRATION OF A SPECIFIC COMPONENT IN A SUBJECT OF MEASUREMENT

This Application is a U.S. National Phase Application of PCT International Application PCT/JP03/03187.

TECHNICAL FIELD

The present invention relates to a concentration measuring instrument of measuring concentrations of glucose, cholesterol, ethanol, the derivatives of cholesterol, etc. which are contained in subjects of measurement, such as living body tissues.

BACKGROUND ART

A variety of methods have been proposed which measure specific components in specimens, particularly in living bodies and solutions using an attenuated total reflectance (hereinafter referred to as ATR) measuring instrument.

For example, in Japanese Patent Laid-Open No. 9-113439, there is proposed a method of measuring the blood sugar level using a transparent ATR device 51 having a pair of parallel reflecting surfaces opposing each other in which measurement is made with upper and lower lips 52, as a specimen, brought into tight contact with the ATR device 51, as shown in FIG. 7. The entire disclosure of Japanese Patent Laid-Open No. 9-113439 is incorporated herein by reference in its entirety. According to this method, the measurement of the blood sugar level is made through the following procedures: inserting an ATR device 51 between upper and lower lips, and getting the same to be hold firmly by the lips; entering light into the ATR device 51 so that the light is allowed to undergo total reflection repeatedly at the interface between each reflection surface of the ATR device 51 and the lips 52, as shown by the broken line in FIG. 7; and analyzing the light that oozes out of the ATR device 51.

In BME, Vol. 5, No. 8 (Japan ME Society, 1991), there is proposed a method which measures the blood sugar level, the concentration of ethanol in blood, etc. using an ATR device made up of ZnSe optical crystal etc. In the method, measurements are made through the following procedures: bringing the ATR device into tight contact with lip mucosa; entering a laser light with a wavelength of 9 to 11 microns into the ATR device and allowing the light to undergo multiple reflection inside the ATR device; and analyze the absorbed and scattered light. The entire disclosure of BME, Vol. 5, No. 8 (Japan ME Society, 1991) is incorporated herein by reference in its entirety. According to this method, concentrations of specific components such as glucose, ethanol and cholesterol can be measured non-invasively and in real time. This method is to apply evanescent light (known as ooze-out light) to a quantitative analysis. Only a very small quantity of the light traveling in the ATR device actually enters lips, and the light having entered the lips is affected by components in the body fluid existing in the lips. For example, in glucose, its light absorption peaks at a wave number of 1080 $cm^{-1}$; therefore, when applying light with the above wave number to a living body, the quantity of the light absorption of glucose changes depending on the glucose concentration in the living body. Accordingly, if the quantity of the light returned from the living body is measured, the change in quantity of the light absorption of a component in body fluid with change in the concentration of the component can be detected, in other words, the concentration of the component can be obtained.

When measuring the absorbance of a substance surface with an ATR measuring instrument and calculating the concentration of the same using the measured absorbance, the measuring method shown in FIG. 8 has been commonly used.

First, in the background measuring step, the measurement of background is made by entering light emitted by a light source into the ATR device, carrying out spectrometry of a reference, such as air or deionized water, while keeping the ATR device out of contact with a sample as a subject of measurement, and storing the measured results in a memory (S8). The reasons for the background measurement are to correct the wavelength characteristics of a light source and a photodetector and to ensure an accurate absorbance measurement or concentration calculation even after their characteristics have changed with time.

Then, the sample as a subject of measurement is set so that it comes in contact with the ATR device (S9) and measurement is made for the sample (S10).

Calculation is carried out according to the following equation, $Log_{10}$ (Ib/Im), where Ib represents a detected signal from the photodetector at the time of background measurement and Im a detected signal from the photodetector at the time of measurement for the sample. The calculated value is commonly referred to as absorbance. Since absorbance correlates with concentration of a specific components in a sample, if a calibration curve of absorbance and concentration is prepared in advance, the concentration of a specific component in the sample can be estimated from the calculated absorbance (S11).

The conventional ATR measuring instruments described above, however, have the following problems.

When the surface of the ATR device is contaminated or the residues left at the last measurement adhere on the surface of the device at the time of background measurement, the accuracy of the measurement for specific components decreases.

For example, when measuring the glucose concentration in lip mucosa, if the mouse is not sufficiently rinsed, components of teas, juices or the like remain on the lip mucosa, which has an adverse effect on the measured results.

DISCLOSURE OF THE INVENTION

The present invention has been made in the light of the above described problems. Accordingly, the object of the invention is to provide a concentration measuring instrument, and a method of measuring the concentration of a specific component in a subject of measurement which enables a highly accurate measurement of the concentration of a specific component in a subject of measurement even when its concentration measuring contact is contaminated by drinks etc. adhering on its surface.

To solve the above problems, a first aspect of the present invention is a concentration measuring instrument, comprising:

a main body that has a concentration measuring contact, a light source that emits light and enters the light into the concentration measuring contact, and a photodetector; and judging means that calculates the difference between a non-contact measured value, a value, measured by the photodetector while keeping a subject of measurement out of contact with the concentration measuring contact, of the quantity of light which is emitted and entered by the light source into the concentration measuring contact, passed through or oozed from the concentration measuring contact to the outside thereof and returned to the concentration measuring contact and a predetermined reference value, a value, measured by the photodetector while keeping the concentration measuring contact clean, of the quantity of the light which is emitted and entered by the light source into the concentration measuring contact, passed through or oozed from the concentration measuring contact to the outside thereof and returned to the concentration measuring contact, and judges whether the calculation of the concentration of a specific component in the subject of measurement is effective or not by comparing the calculated difference with a predetermined threshold.

A second aspect of the present invention is the concentration measuring instrument according to the first aspect of the present invention, further comprising calculating means, wherein the photodetector (6) measures, while keeping the subject of measurement in contact with the concentration measuring contact (2), the quantity of light which is emitted and entered by the light source (1) into the concentration measuring contact (2), passed through the concentration measuring contact (2) into a subject of measurement, transmitted in the subject of measurement, and returned to the concentration measurement contact, when the judging means (8) judges the calculation of the concentration of a specific component in the subject of measurement to be effective, and the calculating means (10) calculates the concentration of a specific component in the subject of measurement based on a contact measured value, a value obtained by making measured while keeping the subject of measurement in contact with the concentration measuring contact (2).

A third aspect of the present invention is the concentration measuring instrument according to the first aspect of the present invention, further comprising indicating means, wherein the indicating means gives a message that indicates the surface of the concentration measuring contact should be cleaned, when the judging means judges the calculation of the concentration of a specific component in the subject of measurement to be ineffective.

A fourth aspect of the present invention is a concentration measuring instrument, including:

a main body that has a concentration measuring contact, a light source that emits light and enters the light into the concentration measuring contact, and a photodetector; and judging means that calculates the difference between (1) a non-contact measured value, a value, measured by the photodetector, of the quantity of light which is emitted and entered by the light source into the concentration measuring contact once brought into contact with the subject of measurement and then kept out of contact with the same, passed through or oozed from the concentration measuring contact to the outside thereof and returned to the concentration measuring contact and (2) a predetermined reference value, a value, measured by the photodetector while keeping the concentration measuring contact clean, of the quantity of light which is emitted and entered by the light source into the concentration measuring contact, passed through or oozed from the concentration measuring contact to the outside thereof and returned to the concentration measuring contact, and A fifth aspect of the oresent invention is the concentration measuring instrument of the fourth aspect of the present invention, further including calculating means, wherein the photodetector measures, while keeping the subject of measurement in contact with the concentration measuring contact, the quantity of light which is emitted and entered by the light source into the concentration measuring contact, passed through the concentration measuring contact into the subject of measurement, transmitted in the subject of measurement, and returned to the concentration measurement contact and compares the calculated difference with a predetermined threshold so as to judge whether the calculation of the concentration of a specific component in the subject of measurement is effective or not.

A fifth invention is the concentration measuring instrument of the fourth invention, further including calculating means (10), wherein the photodetector (6) measures, while keeping the subject of measurement (2) in contact with the concentration measuring contact (2), the quantity of light which is emitted and entered by the light source (1) into the concentration measuring contact (2), passed through the concentration measuring contact (2) into the subject of measurement, transmitted in the subject of measurement, and returned to the concentration measurement contact (2) and when the judging means judges the calculation of the concentration of a specific component in the subject of measurement to be effective, the calculating means calculates the concentration of the specific component in the subject of measurement based on a contact measured value, which is a value measured while keeping the subject of measurement in contact with the concentration measuring contact.

A sixth aspect of the present invention is the concentration measuring instrument of the fourth aspect of the present invention, further including indicating means, wherein the indicating means gives a message that indicates the subject of measurement should be cleaned, when the judging means judges the calculation of the concentration of a specific component in the subject of measurement to be ineffective.

A seventh aspect of the present invention is a concentration measuring instrument, including:

a main body that has a concentration measuring contact, a light source that emits light and enters the light into the concentration measuring contact and a photodetector;

input means that inputs (1) a contact-measured value, a value, measured by the photodetector, of the quantity of light which is emitted and entered by the light source into the concentration measuring contact in contact with a subject of measurement, passed through the concentration measuring contact into the subject of measurement, transmitted in the subject of measurement, and returned to the concentration measuring contact and (2) a non-contact measured value, a value, measured after measuring the contact-measured value by the photodetector and keeping the subject of measurement out of contact with the concentration measuring contact, of the quantity of light which is emitted and entered by the light source into the concentration measuring contact, passed through or oozed from the concentration measuring contact to the outside thereof and returned to the concentration measuring contact;

correcting means that corrects the contact-measured value using the non-contact-measured value; and calculating means that calculates the concentration of a specific component contained in the subject of measurement based on the corrected result.

An eighth aspect of the present invention is the concentration measuring instrument according to anyone of the first to the seventh aspects of the present invention, wherein the concentration measuring contact is an attenuated total reflectance device and the light entered into the concentration measuring contact is evanescent light oozed from the attenuated total reflectance device.

A ninth aspect of the present invention is the concentration measuring instrument according to any one of the first to the seventh asoects of the present invention, wherein the subject of measurement is a living body tissue and the specific component is glucose, ethanol, cholesterol, or the derivative of cholesterol.

A tenth aspect of the present invention is the concentration measuring instrument according to any one of the first to the seventh aspects of the present invention, wherein the photodetector scans the light in the wave number region of 1000 cm$^{-1}$ to 1200 cm$^{-}$ centered at 1100 cm$^{-1}$.

An eleventh aspect of the present invention is the concentration measuring instrument of the seventh aspect of the present invention, wherein the correcting means calculates a value by subtracting the absorbance to the light with a specific wave number, which is calculated from the non-contact measured value, from the absorbance to the light with a specific wave number, which is calculated from the contact-measured value, and the calculating means calculates the concentration of the specific component contained in the subject of measurement based on the value calculated by the correcting means.

A twelfth aspect of the present invention is the concentration measuring instrument according to any one of the first to the sixth aspects of the present invention, wherein the judging means judges the calculation of the concentration of a specific component in the subject of measurement to be ineffective, when the absorbance to the light with a specific wave number which is obtained from the non-contact-measured value is larger than a predetermined value.

A thirteenth aspect of the present invention is the concentration measuring instrument according to any one of the first to the sixth aspects of the present invention, wherein the measurement of the non-contact-measured value is to measure, by the photodetector, the quantities of the p-polarized light component and the s-polarized light component of the light which is emitted and entered by the light source into the concentration measuring contact out of contact with the subject of measurement, passed through or oozed from the concentration measuring contact to the outside thereof, and returned to the concentration measuring contact, the judging means judges whether or not there exists a contaminant adhering on the surface of the concentration measuring contact, based on the measured values of the quantities of the p-polarized light component and the s-polarized light component, and the judgment of whether the calculation of the concentration of a specific component in the subject of measurement is effective or not is to judge whether or not there exists a contaminant adhering on the surface of the concentration measuring contact.

A fourteenth aspect of the present invention is the concentration measuring instrument according to the thirteenth aspect of the present invention, wherein the judging means carries out calculation according to the equation, Ip/Is or $\log_{10}$ (Ip/Is), where Ip represents the measured value of the quantity of the p-polarized light component and Is the measured value of the quantity of the s-polarized light component, and judges that there exists a contaminant adhering on the surface of the concentration measuring contact, when the calculated value is the same as or more than a given value.

A fifteenth aspect of the present invention is the concentration measuring instrument according to the fourteenth aspect of the present invention, wherein the judging means judges that there exists no contaminant adhering on the surface of the concentration measuring contact when the value of Ip/Is is in the range of 0.9 to 1.1.

A sixteenth aspect of the present invention is the concentration measuring instrument according to the thirteenth aspect of the present invention, wherein the judging means carries out calculation according to the equation, Is/Ip or $\log_{10}$ (Is/Ip), where Ip represents the measured value of the quantity of the p-polarized light component and Is the measured value of the quantity of the s-polarized light component, and judges that there exists a contaminant adhering on the surface of the concentration measuring contact, when the calculated value is the same as or less than a given value.

A seventeenth aspect of the present invention is the concentration measuring instrument according to the sixteenth aspect of the present invention, wherein the judging means judges that there exists no contaminant adhering on the surface of the concentration measuring contact when the value of Is/Ip is in the range of 0.9 to 1.1.

An eighteenth aspect of the present invention is a method of measuring the Image Page 9 concentration of a specific component in a subject of measurement utilizing the main body of a concentration measuring instrument that has a concentration measuring contact, a light source that emits light and enters the light into the concentration measuring contact and a photodetector, including:

a non-contact measuring step of measuring, by the photodetector while keeping the subject of measurement out of contact with the concentration measuring contact, the quantity of light which is emitted and entered by the light source into the concentration measuring contact, passed through or oozed from the concentration measuring contact to the outside thereof and returned to the concentration measuring contact; and a judging step of judging whether the calculation of the concentration of the specific component in the subject of measurement is effective or not by comparing with a predetermined threshold a calculated difference obtained by subtracting a predetermined reference value, a value, measured by the photodetector while keeping the concentration measuring contact clean, of the quantity of light which is emitted and entered by the light source into the concentration measuring contact, passed through or oozed from the concentration measuring contact to the outside thereof and returned to the concentration measuring contact from a non-contact measured value, a value measured in the non-contact measuring step.

A nineteenth aspect of the present invention is a method of measuring the concentration of a specific component in a subject of measurement utilizing the main body of a concentration measuring instrument that has a concentration measuring contact, a light source that emits light and enters the light into the concentration measuring contact and a photodetector, including:

a non-contact measuring step of measuring by the photodetector the quantity of light which is emitted and entered by the light source into the concentration measuring contact which is once brought into contact with the subject of measurement and then kept out of contact with the same, passed through or oozed from the concentration measuring contact to the outside thereof and returned to the concentration measuring contact; and a judging step of judging whether the calculation of the concentration of a specific component in the subject of measurement is effective or not by comparing with a predetermined threshold a calculated difference obtained by subtracting a predetermined reference value, a value, measured by the photodetector while keeping the concentration measuring contact clean, of the quantity of light which is emitted and entered by the light source into the concentration measuring contact, passed through or oozed from the concentration measuring contact to the outside thereof and returned to the concentration measuring contact from a non-contact measured value, which is a value measured in the non-contact measuring step.

A twentieth aspect of the present invention is a method of measuring the concentration of a specific component in a subject of measurement, including:

a contact measuring step of measuring by the photodetector the quantity of light which is emitted and entered by the light source into the concentration measuring contact in contact with the subject of measurement, passed through the concentration measuring contact into the subject of measurement, transmitted in the subject of measurement, and returned to the concentration measuring contact;

a non-contact measuring step of measuring by the photodetector the quantity of light which is emitted and entered by the light source into the concentration measuring contact, which is kept out of contact with the subject of measurement after the contact measuring step, passed through or oozed from the concentration measuring contact to the outside thereof, and returned to the concentration measuring contact; and a calculating step of calculating, after correcting the measured result obtained in the contact measuring step with the measured result obtained in the non-contact measuring step, the concentration of the specific component in the subject of measurement based on the corrected result.

DESCRIPTION OF SYMBOLS

1 Light Source
2 Concentration Measuring Contact
3 Light Input Portion
4 Contact Portion
5 Light Output Portion
6 Photodetector
7 Polarizer
51 ATR device
52 Lips

BEST MODE FOR CARRYING OUT THE INVENTION

In the following, embodiments of the present invention will be described with reference to the accompanying drawings.

(Embodiment 1)

First, a first embodiment will be described.

Figure 1:
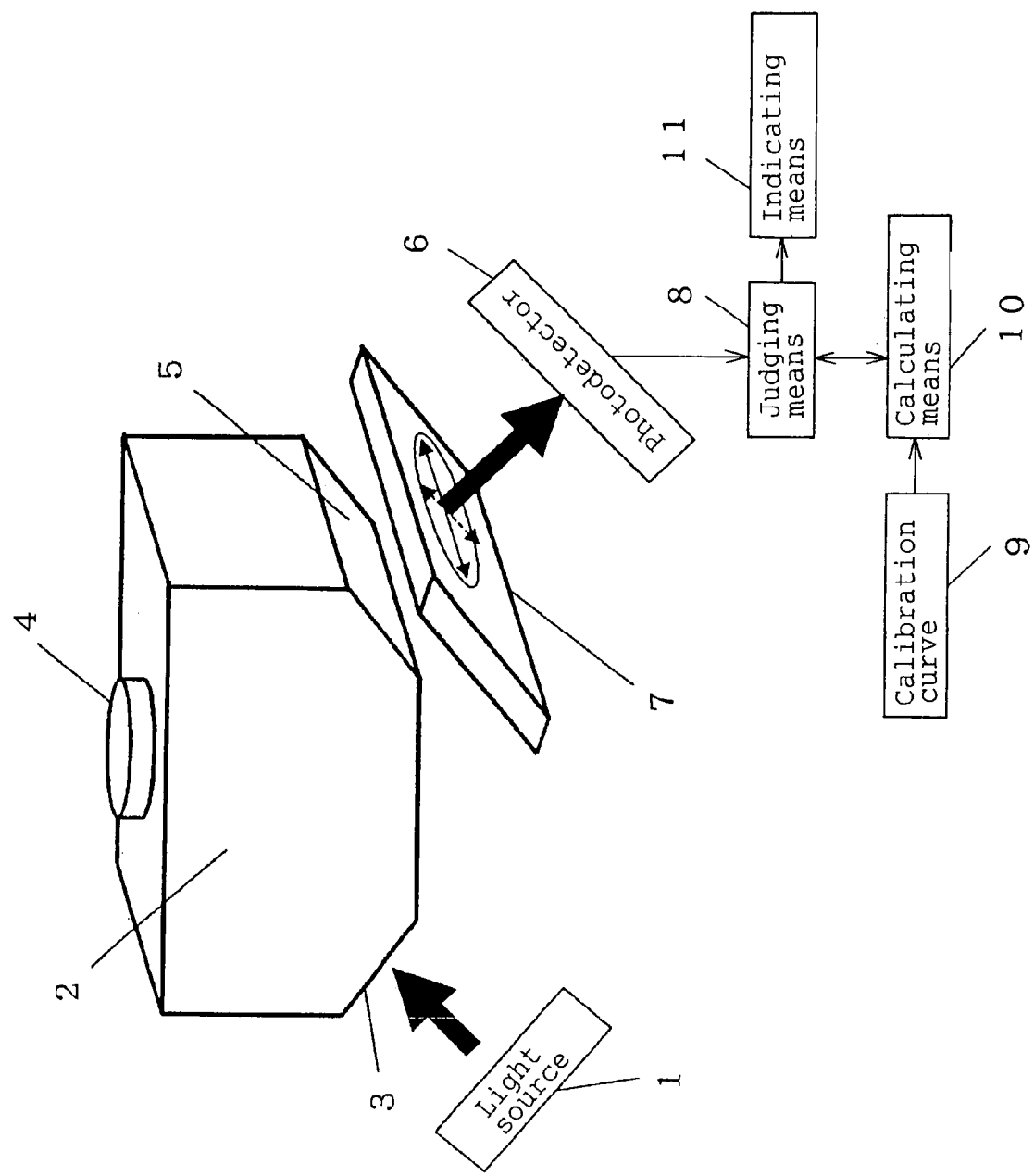
FIG. 1 is a schematic diagram of a concentration measuring instrument which is used in a method of measuring the concentration of a specific component in a specimen in accordance with one embodiment of the present invention.

FIG. 1 is a schematic diagram of a concentration measuring instrument which is used in a method of measuring the concentration of specific components in subjects of measurement in accordance with one embodiment of the invention.

With this embodiment, one case will be described in which a concentration of glucose, as a specific component in a subject of measurement, is measured.

As a light source 1, a light source that emits mid-infrared light is used. In this embodiment, a SiC light source is used as the light source 1. The SiC light source is particularly suitable for making concentration measurements for substances whose absorption wave number is in the fingerprint region (mid-infrared region) of, for example, 1080 cm$^{-1}$ and 1033 cm$^{-1}$.

As a material for a concentration measuring contact 2, is preferably used a material which is capable of transmitting mid-infrared light, chemically stable and excellent in mechanical strength. In this embodiment, germanium is used as the material for the concentration measuring contact 2.

A contact portion 4 is brought into contact with a subject of measurement. For example, when measuring the concentration of a glucose solution, the glucose solution is dropped onto the contact portion 4 so that the solution covers the entire surface of the contact portion 4. The glucose solution never overflows the contact portion 4, due to the effect of its surface tension, and a suitable amount of solution required for the concentration measurement is kept on the contact portion 4, which allows stable measurement of the glucose concentration in the solution.

When the subject of measurement is a living body, the living body is brought into tight contact with the contact portion 4. In this case, the area of the portion which is in tight contact with the living body is preferably 2 cm$^2$ or less. When the area is about 2 cm$^2$ or less, the contact portion eats deeper into the living body and its contact with the living body becomes much tighter, which allows stable measurements. As for the portion of the living body which is brought into tight contact with the contact portion 4, the portion whose stratum corneum is thin is preferable, specifically proximal nail wall at the base of a finger-nail, lips and oral mucosa are preferable.

Preferably the shape of the contact portion 4 is, but not limited to, approximately circular. The reason is that when the subject of measurement is a living body, the circular shape lessens the pain the subject suffers at the time of measurement. More preferably the periphery of the contact portion 4 is provided with a chambered portion or a rounded portion, because providing such portions much lessens the pain of the subject.

As a photodetector 6, an MCT photodetector is used in this embodiment.

A polarizer 7 functions to take out a specific component of polarized light. In this embodiment, a wire grid polarizer is used in which a plurality of fine slits are provided. Rotating the polarizer 7 makes it possible to arbitrarily set the component of polarized light that reaches the photodetector 6 to s-polarized light or p-polarized light. The position of the polarizer 7 is not limited to the position shown in FIG. 1, it has only to be positioned on the optical path between the light source 1 and the photodetector 6.

In FIG. 1, the direction shown by the solid line on the polarizer 7 denotes the vibration direction of the s-polarized light component and the direction shown by the broken line the vibration direction of the p-polarized light component. The polarizer 7 transmits light in the same vibration direction alone; therefore, measurement of the p-polarized light component, after measurement of the s-polarized light component in which the component of polarized light is set to the direction shown by the solid line, can be made just by rotating the polarizer 7 at an angle of 90 degrees.

Providing, for example, spectroscopic means (not shown in the figure) between the light source 1 and the concentration measuring contact 2 is preferable, because it allows the measurement of the wavelength-spectral characteristics of the specific component and obtaining the absorption characteristics of the same at different wavelengths. The spectroscopy, FT-IR method, which uses an interferometer is particularly preferable as spectroscopic means, because it allows highly sensitive measurement.

Judging means 8 judges whether the calculation of the concentration of the specific component in a subject of measurement is effective or not.

Calculating means 10 calculates the concentration of a glucose solution from the measurements obtained by the photodetector 6 utilizing a calibration curve 9. As the calculating means 10, a microcomputer or a personal computer made up of a CPU and a memory is used.

The calibration curve 9 is a collection of data obtained through the following procedures: measuring in advance concentrations of glucose solutions, whose concentrations are already known, by the method of measuring the concentration of specific components in the specimen in accordance with the embodiment of the present invention; and getting the measured results to have one to one correspondence to the known concentrations of glucose solutions. The calibration curve 9 is stored in, for example, the above described microcomputer or personal computer in advance.

The indicating means 11 indicates measurement results obtained at the photodetector 6, messages to the operator and the like.

Figure 2:
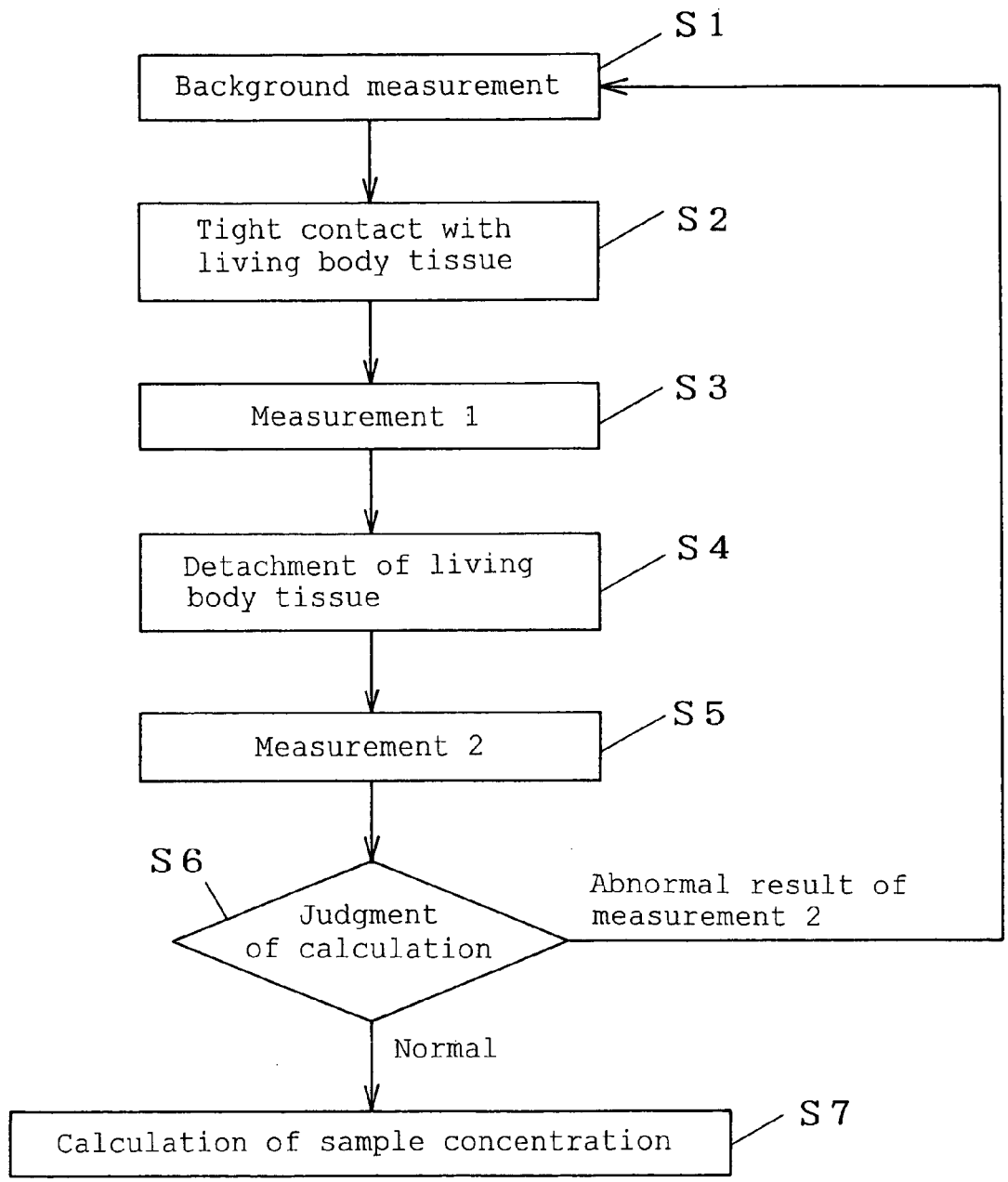
FIG. 2 is a schematic diagram showing the measurement flow of the method of measuring the concentration of the specific component in the specimen.

Then, the method of measuring the concentration of specific components in the specimen in accordance with this embodiment, which uses the above described measuring instrument, will be described taking the case in which a glucose concentration is measured through subject's lip mucosa. FIG. 2 is a schematic diagram showing the measurement flow of the method of measuring the concentration of specific components in the specimen in accordance with this embodiment.

As shown in FIG. 2, first, background is measured (S1). The measurement of background is made, while keeping subject's lip mucosa out of tight contact with the contact portion 4 shown in FIG. 1, through the following procedures: entering light emitted by the light source 1 into the light input portion 3 of the concentration measuring contact 2; and measuring the quantity of light, by the photodetector 6, which is passed through the contact portion 4 to its outside, returned back to the contact portion 4, and output from the light output portion 5 to the outside of the concentration measuring contact 2. In this measurement, the polarizer 7 may be set to p-polarized light or s-polarized light. Spectrometry may be made with the entire surface of the contact portion 4 covered and moistened with water. Then, the subject's lip mucosa is brought into contact with the contact portion 4 (S2) and a first spectrometry (measurement 1) is made (S3). This measurement is made with the polarizer 7 set to the same polarized light component as that of background measurement. Like the case of background measurement, the measurement is made through the following procedures: entering light emitted by the light source 1 into the light input portion 3 of the concentration measuring contact 2; and measuring the quantity of light, by the photodetector 6, which is passed through the contact portion 4 into the lip mucosa of a subject, returned back to the contact portion 4 after transmitted in the lip mucosa, and output from the light output portion 5 to the outside of the concentration measuring contact 2. Then, the calculating means 10 carries out calculation according to the equation, $\log_{10}$ (Ib/Im1), where Ib represents the value obtained by the background measurement and Im1 the value obtained by the first spectrometry. And the calculated value is taken as absorbance of the lip mucosa.

Then, the contact portion 4 is detached from the lip mucosa (S4) and a second spectrometry (measurement 2) is made (S5) in the same manner as the measurement of background without wiping away saliva and contaminants adhering to the surface of the contact portion 4. The calculating means 10 carries out calculation according to the equation, $\log_{10}$ (Ib/Im2), where Im2 represents the value obtained by the second spectrometry, to give absorbance of the saliva or a contaminant.

Figure 3:
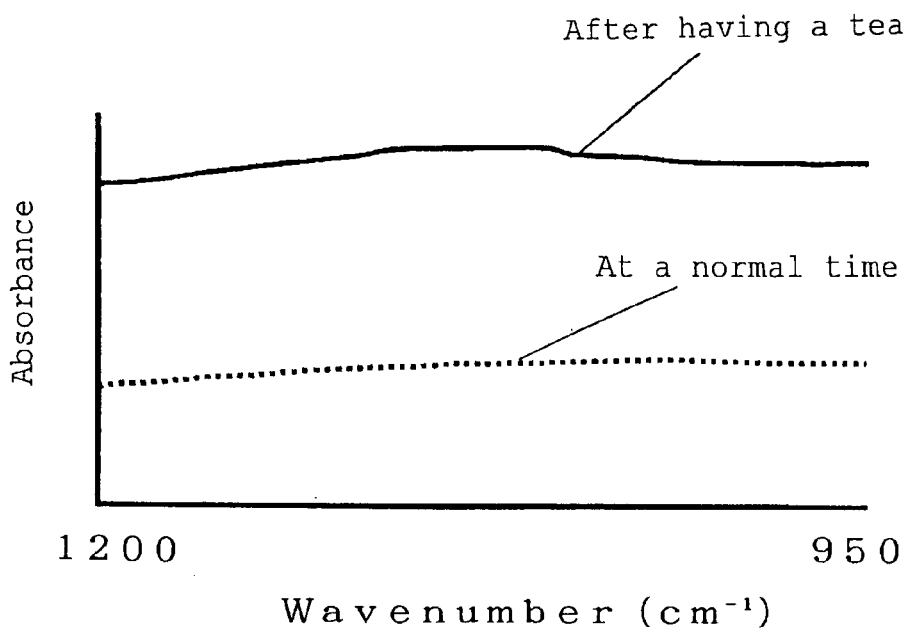
FIG. 3 illustrates characteristic curves showing the spectral characteristics in the second spectrometry of the method of measuring the concentration of the specific component in the specimen.

One example of spectral characteristics obtained by carrying out calculation according to the equation, $\log_{10}$ (Ib/Im2), is shown in FIG. 3. When measurement is made properly, since the most part of the components of the body fluid remaining on the contact portion is saliva, the spectral characteristics are those at a normal time shown in FIG. 3. The term "characteristics at a normal time" herein used means characteristics obtained by making spectrometry with the surface of the contact portion 4 moistened with water. However, when making spectrometry through oral mucosa of a subject with the oral mucosa not given a sufficient rinse after the subject drinks tea, juice or the like, the spectral characteristics are those after having tea shown in the same figure and sometimes largely different from those at a normal time. It is known from the figure that, compared with the characteristics at a normal time, the absorbance after having tea is large as a whole, in addition, the spectral line shape is changed in the wave number region of about 1200 $cm^{-1}$ to about 1000 $cm^{-1}$ centered at about 1100 $cm^{-1}$ where the light absorption of glucose reaches a peak. The value of the absorbance is about 0.02±0.02 at a normal time and about 0.06±0.02 after having tea.

Figure 4:
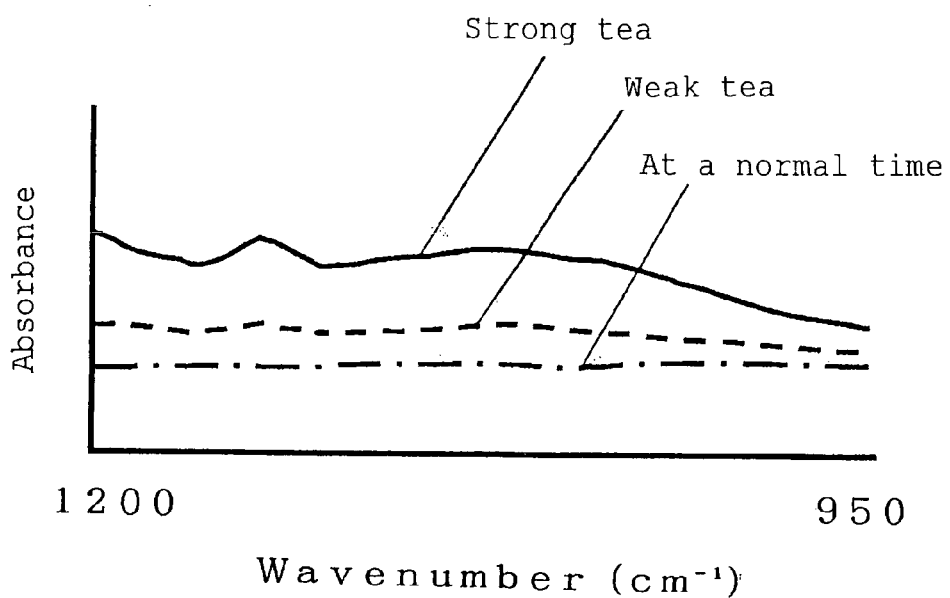
FIG. 4 illustrates characteristic curves showing the spectral characteristics of teas and water.

The absorbance curves of tea and water are shown in FIG. 4. In the same figure, the one dot-dash line represents the absorbance at a normal time, the broken line the absorbance of relatively weak tea, and the solid line the absorbance of relatively strong tea. The term "the absorbance at a normal time" herein used means the spectral characteristics obtained by making spectrometry with the surface of the contact portion 4 moistened with water. As shown in the figure, it is apparent that in the spectral characteristics after having tea, the absorbance and the change in spectral line shape are large, compared with the spectral characteristics at a normal time, and the higher the concentration of tea, the larger the absorbance and the change in spectral line shape become. From this, it is conceived that because of the effects of the absorbance of tea, the measured results different from those at a normal time are obtained when making the second spectrometry after a subject has the tea, as shown in FIG. 3, and the calculation of a glucose concentration is adversely affected.

Accordingly, in cases where the absorbance or the spectral line shape, which is obtained by calculating spectral characteristics after ending the second spectrometry, is changed largely and the absorbance to the light with a specific wave number is larger than a given value, it is very likely that the first spectrometry has been made with a component obstructive to the spectrometry contained between the lip mucosa and the contact portion 4. Thus, the judging means 8 judges that the measured results in the first spectrometry are ineffective (S6).

In other words, the judging means 8 calculate the difference between the spectral characteristics and absorbance at a normal time and those obtained by the second spectrometry, which are shown in FIGS. 3 and 4. The spectral characteristics and absorbance at a normal time shown in FIGS. 3 and 4 are those calculated from the measured values obtained through the following procedures: entering light emitted by the light source 1 into the concentration measuring contact 2 while keeping the concentration measuring contact 2 clean; measuring the quantity of the light, by the photodetector 6, that is passed through the concentration measuring contact 2 to its outside and returned to the concentration measuring contact 2 again. And these spectral characteristics and absorbance are obtained in advance.

The judging means 8 judges whether the calculation of the concentration of a specific component in a subject of measurement is effective or not by comparing the difference with the predetermined threshold. Specifically, if the difference is larger than the predetermined threshold, the judging means 8 judges the calculation of the concentration of a specific component in a subject of measurement to be ineffective, whereas if the difference is smaller than the predetermined threshold, it judges the calculation of the concentration of a specific component in a subject of measurement to be effective.

The spectral characteristics and absorbance at a normal time of this embodiment shown in FIGS. 3 and 4 are examples of reference values of this invention.

When the measuring means 8 judges the calculation of the concentration of a specific component in a subject of measurement is ineffective, indicating means 11 gives a message that indicates the subject should give his or her oral mucosa a good rinse. With this indication, measurement can be made again after the oral mucosa is rinsed with cold or warm water, which enables accurate measurement of a glucose concentration. After rinsing the oral mucosa, measurement is started again from the background measurement, S1.

When the measuring means 8 judges the calculation of the concentration of a specific component in a subject of measurement is effective, the calculating means 10 calculates, using the calibration curve 9, the concentration of the glucose solution from the absorbance of the first spectrometry (measurement 1) obtained by making the first spectrometry (measurement 1) and the background measurement (S7).

Figure 5:
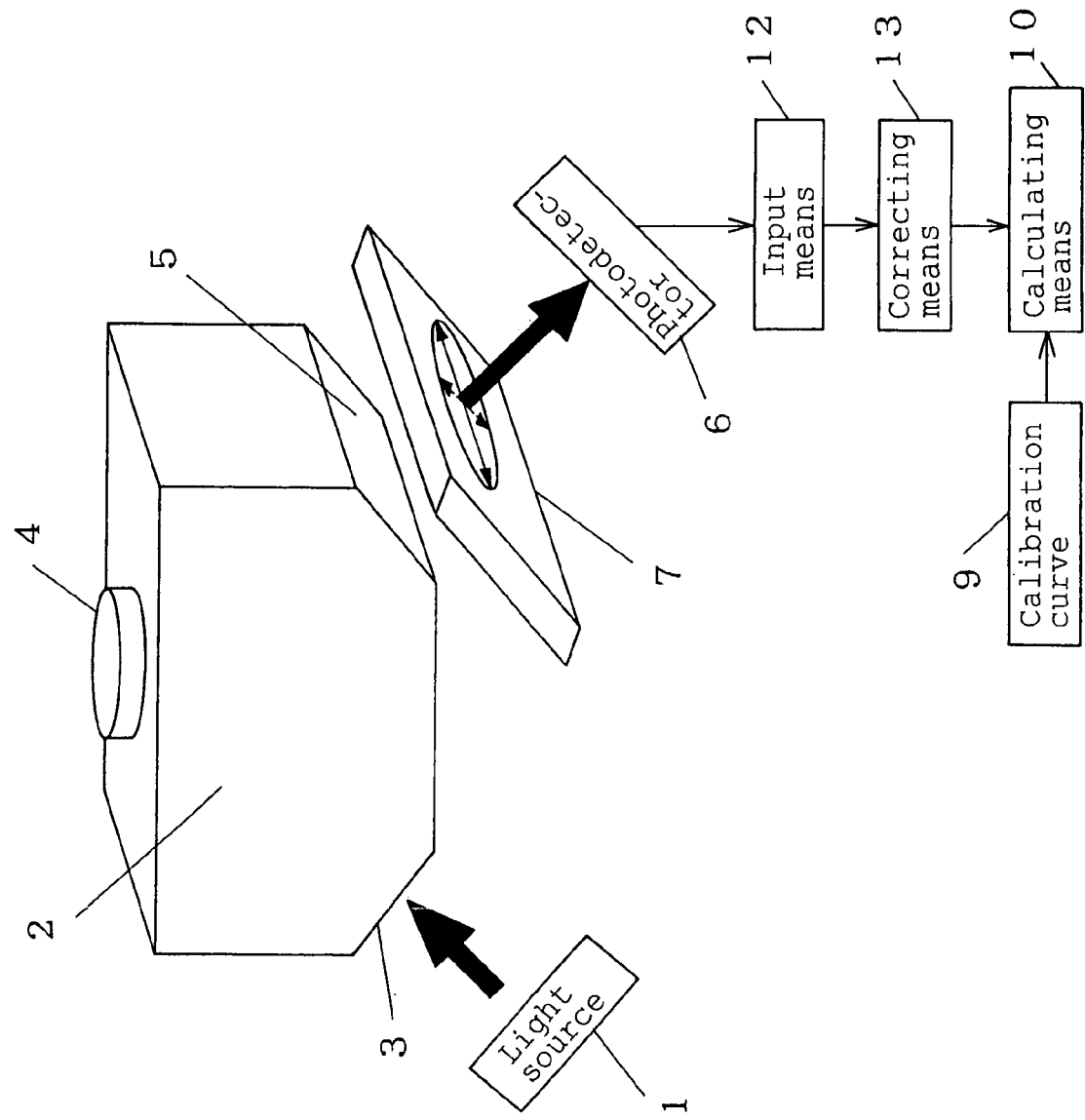
FIG. 5 is a schematic diagram of another concentration measuring instrument which is used in a method of measuring the concentration of a specific component in a specimen in accordance with one embodiment of the present invention.

The measured value Im1 obtained by the first spectrometry may be corrected by calculating the effects of the obstructing component based on the measured value Im2 obtained by the second spectrometry. FIG. 5 shows a concentration measuring instrument that is capable of making such corrections. In the figure, the same parts as those of FIG. 1 are denoted by the same reference numerals and a detailed description of them will be omitted.

Input means 12 inputs the measured value obtained at the time of background measurement and the measured values Im1, Im2 obtained by the first and second spectrometry from the photodetector 6. The input means 12 calculates the absorbance to the light with a specific wave number in the first spectrometry from the measured value Im1 obtained by the first spectrometry and the measured value obtained by the background measurement. Further, the input means 12 calculates the absorbance to the light with a specific wave number in the second spectrometry from the measured value Im2 obtained by the second spectrometry and the measured value obtained by the background measurement.

Then, correcting means 13 calculates a value by subtracting the absorbance to the light with a specific wave number, which is calculated from the measured value Im2 obtained in the second spectrometry, from the absorbance to the light with a specific wave number, which is calculated from the measured value Im1 obtained in the first spectrometry.

Calculating means 10 calculates the concentration of a glucose solution, that is, the concentration of a specific component from the value calculated by the correcting means 13 using a calibration curve 9. Doing this enables the effects of obstructing components to be gotten rid of, and hence the accurate glucose concentration to be obtained.

The embodiment 1 has been described taking the case where the quantity of polarized light of a specific component is measured using a polarizer 7, but the method of measuring such quantity of light is not limited to this. Without the polarizer 7, the same effect as this embodiment can be obtained. However, since the component of p-polarized light oozes deeper into a subject of measurement than that of s-polarized light, if the instrument is provided with the polarizer 7 and the quantity of the p-polarized light component is measured using the polarizer 7, the concentration of a specific component can be obtained with a higher accuracy.

The calibration curve 9 may be a table in which the measured results are allowed to have one to one correspondence to the known concentrations of glucose solutions or a mathematical equation by which the measured results are allowed to have one to one correspondence to the known concentrations of glucose solutions.

As described with FIG. 3, since light absorption of glucose reaches a peak in the wave number region of about 1200 $cm^{-1}$ to about 1000 $cm^{-1}$ centered at about 1100 $cm^{-1}$, if the wave number region of about 1200 $cm^{-1}$ to about 1000 $cm^{-1}$ centered at about 1100 $cm^{-1}$ is scanned in the background measurement, the first and second spectrometry, the glucose concentration can be measured with a higher accuracy.

Further, this embodiment has been described taking the case where a SiC light source is used as the light source 1, but the light source is not limited to this. For example, tungsten is preferably used as the light source 1. A quantum cascade laser is more preferably used as the light source 1. These light sources are particularly suitable for measuring the concentrations of substances, such as glucose, whose absorption wave numbers are in the fingerprint region (mid-infrared region) of about 1080 cm$^{-1}$ to about 1033 cm$^{-1}$, like the case where a SiC light source is used.

Further, this embodiment has been described taking the case where germanium is used as the material for the concentration measuring contact 2, but the material for the concentration measuring contact 2 is not limited to this. Silicon, which is capable of transmitting mid-infrared light, chemically stable and excellent in mechanical strength, can also be used as the material for the concentration measuring contact 2.

When using silicon as the material for the concentration measuring contact 2, a silicon single crystal substrate is used which is transparent to light with a wavelength of about 1.1 to about 10 microns. Silicon having small content of impurities, such as boron and phosphorus, and having resistivity of about 100 Ωcm or more is particularly preferable. Silicon having resistivity of about 1500 Ωcm or more is much more preferable. The silicon having such high resistivity has high transmissivity at infrared wavelength of about 9 to about 10 microns, and it is preferably used when measuring the concentration of substances, such as glucose, whose absorption region is in this wavelength band.

Preferably an antireflection film is provided on the surface of the light input portion 3. As a material for the antireflection film, diamond-like carbon (DLC) or ZnSe is used. The thickness of the antireflection film is preferably about 1.1 to about 1.3 microns, more preferably about 1.2 microns.

Preferably an antireflection film is provided on the surface of the light output portion 5, like the light input portion 3.

Further, this embodiment has been described taking the case where an MCT photodetector is used as the photodetector 6, but the photodetector is not limited to this. A pyroelectric sensor may also be used as the photodetector 6.

Further, this embodiment has been described taking the case where a wire grid polarizer is used as the polarizer 7, but the polarizer is not limited to this. An interference filter type of polarizer, which transmits the p-polarized light component and reflects the s-polarized light component, may also be used as the polarizer 7.

(Embodiment 2)

In the method of measuring the concentration of a specific component in accordance with this embodiment, a step of judging whether or not there exists a contaminant adhering on the surface of the concentration measuring contact 2 is carried out before making background measurement. This step is to prevent the measured results from being adversely affected by the residues of the last measurement adhering on the surface of the contact portion 4, when making background measurement with the contact portion 4 contaminated with them.

First, the polarizer 7 is used to allow the light of s-polarized component to pass and spectrometry of the s-polarized light component is made with lip mucosa, as a subject of measurement, not brought into tight contact with the contact portion 4. Then the polarizer 7 is rotated at an angle of 90 degrees to allow the light of p-polarized component to pass and spectrometry of the p-polarized component is made.

Then, the judging means 8 carries out calculation according to the equation, Ip/Is, where Ip represents the measured value of the quantity of the p-polarized light component and Is the measured value of the quantity of the s-polarized light component. Calculating Ip/Is allows the evaluation of light absorption characteristics of the contaminants adhering on the surface of the contact portion 4.

Figure 6:
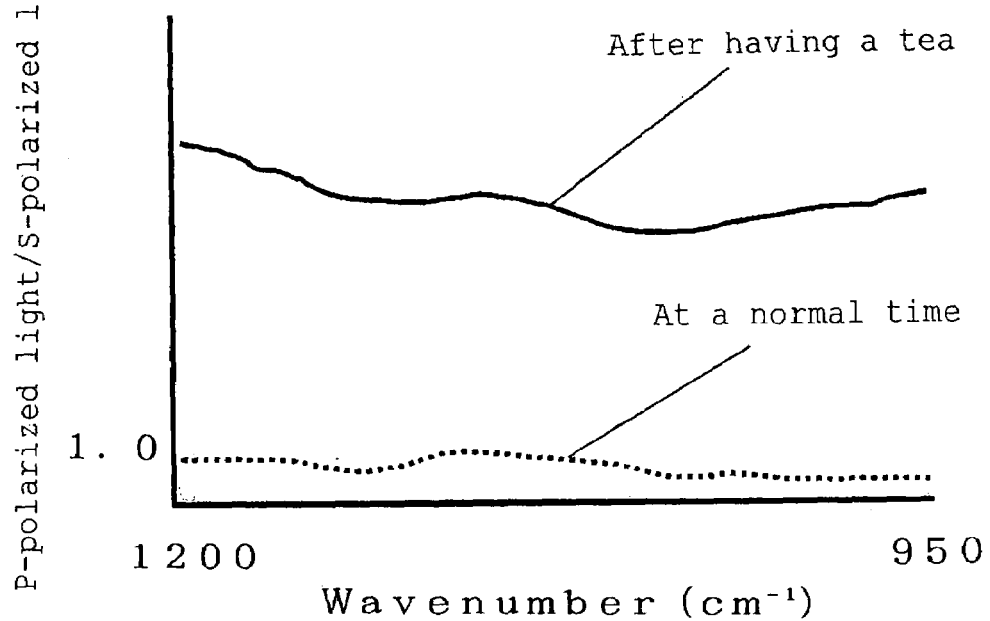
FIG. 6 illustrates characteristic curves showing the spectral characteristics obtained in one step of the method of measuring the concentration of a specific component in a specimen in accordance with another embodiment of the present invention, in which judgment is made whether or not there exists a contaminant adhering to the surface of the concentration measuring contact.
Figure 7:
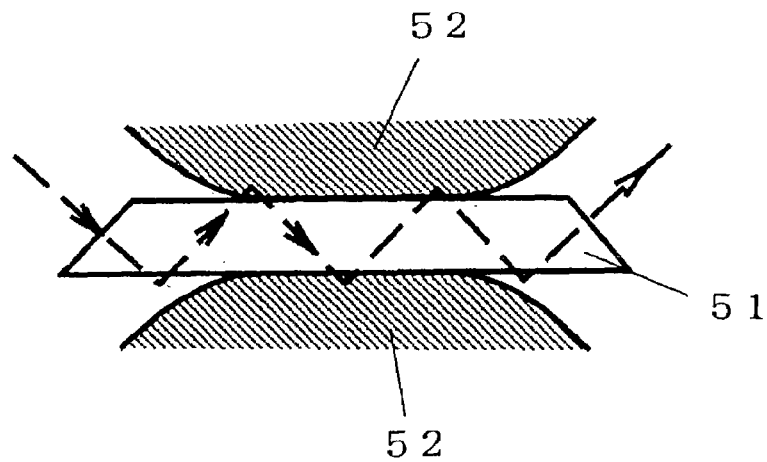
FIG. 7 is a schematic view of a conventional ATR measuring instrument.
Figure 8:
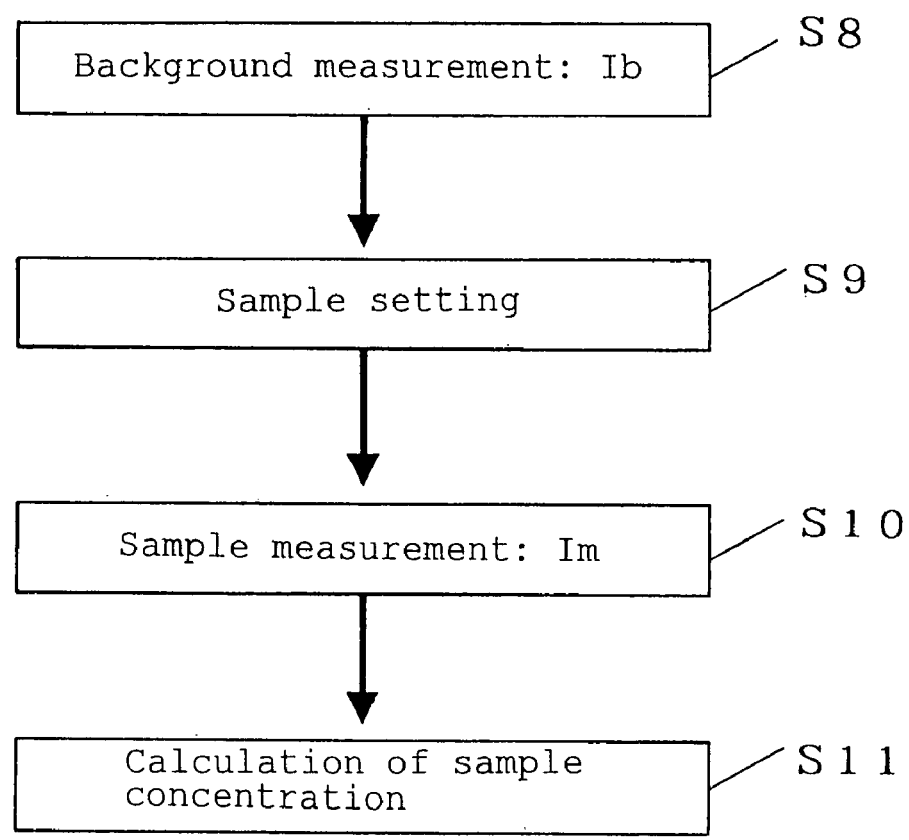
FIG. 8 is a schematic diagram showing the measurement flow of the conventional method of measuring the concentration of a specific component in a specimen.

FIG. 6 shows the spectral characteristics obtained by carrying out calculation according to the equation, Ip/Is. In the same figure, the graph with "at a normal time" shows the spectral characteristics obtained by making spectrometry while keeping the surface of the contact portion 4 clean and moistening the same with water. The graph with "after having atea" shows the spectral characteristics obtained by making spectrometry with the contact portion, which has been brought into tight contact with a person's lip mucosa after the person has tea, kept out of contact with the lip mucosa. It is apparent from the figure that there is a significant difference between the spectral characteristics at a normal time and after having tea.

Accordingly, when the value of Ip/Is is the same as or larger than a given value, the judging means 8 judges that there exists a contaminant adhering on the surface of the contact portion 4. Specifically, when the value of Ip/Is is in the range of about 0.9 to about 1.1, the judging means 8 judges that there exists no contaminant adhering on the surface of the contact portion 4. And when the value of Ip/Is is outside the above range, the judging means 8 judges that there exists a contaminant adhering on the surface of the contact portion 4. Thus, the judging means 8 judges whether or not the calculation of the concentration of a specific component in a subject of measurement is effective.

When the judging means 8 judges that there exists a contaminant adhering on the surface of the contact portion 4, the indicating means 11 gives a message that indicates the surface of the contact portion 4 should be cleaned. If the measurement is made again after the surface of the contact portion 4 is cleaned, the accuracy of the glucose concentration measurement can be improved.

When the judging means 8 judges that there exists no contaminant adhering on the surface of the contact portion 4, the same operation as that of the embodiment 1 is carried out.

In this measurement, it is preferable to set the incident angle θ of the light entered into the contact portion 4 so that the value, z/λ, calculated using the following equation (1) becomes about 0.25 or more.

$$\frac{z}{\lambda} = \frac{1}{2\pi\sqrt{nf^2 \sin^2\theta - nc^2}} \qquad \text{(Mathematical Equation 1)}$$

wherein z represents the depth (unit: micron) to which the light entered into the contact portion oozes into the contaminant adhering on the surface of the contact portion, λ the wavelength (unit: micron) of the light entered into the contact portion, nf the refractive index of the contact portion, θ the incident angle of the light entered into the contact portion, and nc the refractive index of the contaminant.

For example, in cases where the contaminant adhering on the surface of the contact portion is a tea, the wavelength of the light is about 9.6 microns and the refractive index of the tea nc is about 1.24, if germanium, whose refractive index nf is about 4, is used for the contact portion, the incident light θ which satisfies z/λ=0.25 is about 45 degrees. If light is entered into the contact portion at such an incident angle, the absorbance of the contaminant differs largely depending on whether the incident light is the s-polarized light or the p-polarized light. The presence or absence of the contaminant can be detected by the difference in absorbance created depending on whether the incident light is the s-polarized light or the p-polarized light. Specifically, the s-polarized light oozes into the contaminant only to a shallower portion, whereas the p-polarized light oozes into the contaminant to a deeper portion. And the s-polarized light is hardly affected by the concentration of a specific component contained in the contaminant adhering on the surface of the contact portion. In other words, the measurement of the quantity of the s-polarized light corresponds to the measurement of background in the prior art and the measurement of the quantity of the p-polarized light corresponds to the measurement of spectral characteristics of the contaminant in the prior art. Thus, the presence or absence of the contaminant can be detected by measuring the quantities of the s-polarized light and p-polarized light.

This method is effective when the incident angle of the light entered into the contact portion is 45 degrees or less, but preferably the incident angle is larger than critical angle. If the incident angle is smaller than critical angle, the light does not satisfy the total reflection requirements; as a result, the light is scattered in the contaminant adhering on the surface of the contact portion, which decreases the quantity of light returned to the contact portion, and in addition, the optical path difference between the p-polarized light and the s-polarized light is decreased. Experiments showed that when $z/\lambda=0.9$ or more, in other words, when using germanium for the contact portion and setting the incident angle to about 21 degrees or about 20 degrees, particularly satisfactory results were obtained, and when setting the incident angle to about 19 degrees, much more satisfactory results were obtained.

Although this embodiment has been described taking the case where the value, Ip/Is, is used to carry out the step of judging the presence or absence of a contaminant adhering on the surface of the concentration measuring contact, the value is not limited to this. When using a value calculated according to the equation, $\log_{10}$ (Ip/Is), the same effect can be obtained. Further, the judgment may be made using a value calculated according to the equation, Is/Ip or $\log_{10}$ (Is/Ip), and when the value is the same as or smaller than a given value, a contaminant is judged to be present on the surface of the concentration measuring contact. In cases where the value, Is/Ip, is used to judge whether or not there exists a contaminant on the surface of the concentration measuring contact, if the value of Is/Ip is in the range of about 0.9 to about 1.1, the judging means 8 judges that there exists no contaminant adhering on the surface of the concentration measuring contact. And when the value of Is/Ip is outside the above range, the judging means 8 judges that there exists a contaminant adhering on the surface of the concentration measuring contact.

Further, though the embodiment 2 has been described taking the case where the same operation as that of the first embodiment is carried out when the judging means 8 judges that there exists no contaminant adhering on the surface of the contact portion, the operation is not limited to this. When the judging means 8 judges that there exists no contaminant adhering on the surface of the contact portion, the steps 4 and 5 of the embodiment 1 may be omitted.

Further, though the embodiment 2 has been described taking the case where the concentration of glucose, as a specific component in a subject of measurement, is measured, the subject of measurement is not limited to this. The method is effective when measuring the concentration of glucose not only in a glucose solution, but also in blood plasma, a living body, etc. When the specific component in a subject of measurement is a component other than glucose, such as cholesterol, ethanol or the derivative of cholesterol, this embodiment can be effectively applied. However, the specific component in a subject of measurement is changed, the wavelength of light to be measured is also changed.

Specifically, when the specific component of a subject of measurement is cholesterol or the derivative of cholesterol, since the absorption wavelength of cholesterol is 1500 nm or 1700 nm, a light source that emits light with such a wavelength should be used as a light source 1 or a photodetector that detects light with such a wavelength should be used. When the specific component of a subject of measurement is ethanol, since the absorption wave number of ethanol is about 1240 $cm^{-1}$ or about 1400 $cm^{-1}$, a light source that emits light with such a wave number should be used as a light source or a photodetector that detects light with such a wave number should be used. When the specific component of a subject of measurement is different from the above described ones, if a light source that emits light with an absorption wave numbers of the specific component of the subject of measurement is used or a photodetector that detects light with such a wave number is used, the concentration of the specific component in the subject of measurement can be measured, like the above described components.

INDUSTRIAL APPLICABILITY

According to this invention, a concentration measuring instrument and a method of measuring the concentration of a specific component in a subject of measurement can be provided which enables a highly accurate measurement of the concentration of specific components in subjects of measurement even when the concentration measuring contact of a concentration measuring instrument is contaminated with drinks or the like, because the method includes a judging step of judging whether or not there exists a substance, which is obstructive to the measurement of the concentration of specific components, adhering on the surface of the contact portion of the concentration measuring contact.

The invention claimed is:

1. A concentration measuring instrument, comprising:
a main body that has a concentration measuring contact, a light source that emits light and enters the light into the concentration measuring contact, and a photodetector; and
judging means that
calculates the difference between (1) a non-contact measured value, a value, measured by the photodetector while keeping a subject of measurement out of contact with the concentration measuring contact, of the quantity of light which is emitted and entered by the light source into the concentration measuring contact, passed through or oozed from the concentration measuring contact to the outside thereof and returned to the concentration measuring contact and (2) a reference value, a value, measured by the photodetector while keeping the concentration measuring contact clean, of the quantity of the light which is emitted and entered by the light source into the concentration measuring contact, passed through or oozed from the concentration measuring contact to the outside thereof and returned to the concentration measuring contact, and judges whether a calculation of the concentration of a specific component in the subject of measurement is effective or not by comparing the calculated difference with a threshold.

2. The concentration measuring instrument according to claim 1, further comprising calculating means, wherein the photodetector measures, while keeping the subject of measurement in contact with the concentration measuring contact, the quantity of light which is emitted and entered by the light source into the concentration measuring contact, passed through the concentration measuring contact into a subject of measurement, transmitted in the subject of measurement, and returned to the concentration measurement contact, when the judging means judges the calculation of the concentration of a specific component in the subject of measurement to be effective, and the calculating means calculates the concentration of a specific component in the subject of measurement based on a contact measured value, a value obtained by making measurements while keeping the subject of measurement in contact with the concentration measuring contact.

3. The concentration measuring instrument according to claim 1, further comprising indicating means, wherein the indicating means gives a message that indicates the surface of the concentration measuring contact should be cleaned, when the judging means judges the calculation of the concentration of a specific component in the subject of measurement to be ineffective.

4. A concentration measuring instrument, including:

a main body that has a concentration measuring contact, a light source that emits light and enters the light into the concentration measuring contact, and a photodetector; and judging means that calculates the difference between (1) a non-contact measured value, a value, measured by the photodetector, of the quantity of light which is emitted and entered by the light source into the concentration measuring contact once brought into contact with a subject of measurement and then kept out of contact the same, passed through or oozed from the concentration measuring contact to the outside thereof and returned to the concentration measuring contact and (2) a reference value, a value, measured by the photodetector while keeping the concentration measuring contact clean, of the quantity of light which is emitted and entered by the light source into the concentration measuring contact, passed through or oozed from the concentration measuring contact to the outside thereof and returned to the concentration measuring contact, and compares the calculated difference with a threshold so as to judge whether a calculation of the concentration of a specific component in the subject of measurement is effective or not.

5. The concentration measuring instrument according to claim 4, further including calculating means, wherein the photodetector measures, while keeping the subject of measurement in contact with the concentration measuring contact, the quantity of light which is emitted and entered by the light source into the concentration measuring contact, passed through the concentration measuring contact into the subject of measurement, transmitted in the subject of measurement, and returned to the concentration measurement contact and when the judging means judges the calculation of the concentration of a specific component in the subject of measurement to be effective, the calculating means calculates the concentration of the specific component in the subject of measurement based on a contact measured value, which is a value measured while keeping the subject of measurement in contact with the concentration measuring contact.

6. The concentration measuring instrument according to claim 4, further including indicating means, wherein the indicating means gives a message that indicates the subject of measurement should be cleaned, when the judging means judges the calculation of the concentration of a specific component in the subject of measurement to be ineffective.

7. A concentration measuring instrument, incuding:

a main body that has a concentration measuring contact, a light source that emits light and enters the light into the concentration measuring contact and a photodetector;

inputting means that inputs (1) a contact-measured value, a value, measured by the photodetector, of the quantity of light which is emitted and entered by the light source into the concentration measuring contact in contact with a subject of measurement, passed through the concentration measuring contact into the subject of measurement, transmitted in the subject of measurement, and returned to the concentration measuring contact and (2) a non-contact measured value, a value, measured after measuring the contact-measured value by the photodetector and keeping the subject of measurement out of contact with the concentration measuring contact, of the quantity of light which is emitted and entered by the light source into the concentration measuring contact, passed through or oozed from the concentration measuring contact to the outside thereof and returned to the concentration measuring contact;

correcting means that corrects the contact-measured value using the non-contact-measured value; and calculating means that calculates the concentration of a specific component contained in the subject of measurement based on the corrected result.

8. The concentration measuring instrument according to claim 7, wherein the correcting means calculates a value by subtracting the absorbance of the light with a specific wave number, which is calculated from the non-contact measured value, from the absorbance of the light with a specific wave number, which is calculated from the contact-measured value, and the calculating means calculates the concentration of the specific component contained in the subject of measurement based on the value calculated by the correcting means.

9. The concentration measuring instrument according to any one of claims 1 to 7, wherein the concentration measuring contact is an attenuated total reflectance device and the light entered into the concentration measuring contact is evanescent light oozed from the attenuated total reflectance device.

10. The concentration measuring instrument according to any one of claims 1 to 7, wherein the subject of measurement is a living body tissue and the specific component is glucose, ethanol, cholesterol, or the derivative of cholesterol.

11. The concentration measuring instrument according to any one of claims 1 to 7, wherein the photodetector scans the light in the wave number region of about 1000 cm$^{-1}$ to about 1200 cm$^{-1}$ centered at about 1100 cm$^{-1}$.

12. The concentration measuring instrument according to any one of claims 1 to 6, wherein the judging means judges the calculation of the concentration of a specific component in the subject of measurement to be ineffective, when the absorbance to the light with a specific wave number which is obtained from the non-contact-measured value is larger than a predetermined value.

13. The concentration measuring instrument according to any one of claims 1 to 6, wherein
the measurement of the non-contact-measured value is to measure, by the photodetector, the quantities of the p-polarized light component and the s-polarized light component of the light which is emitted and entered by the light source into the concentration measuring contact out of contact with the subject of measurement, passed through or oozed from the concentration measuring contact to the outside thereof, and returned to the concentration measuring contact,
the judging means judges whether or not there exists a contaminant adhering on the surface of the concentration measuring contact, based on the measured values of the quantities of the p-polarized light component and the s-polarized light component, and
the judgment of whether the calculation of the concentration of a specific component in the subject of measurement is effective or not is to judge whether or not there exists a contaminant adhering on the surface of the concentration measuring contact.

14. The concentration measuring instrument according to claim 13, wherein the judging means carries out calculation according to the equation, Ip/Is or $\log_{10}$ (Ip/Is), where Ip represents the measured value of the quantity of the p-polarized light component and Is the measured value of the quantity of the s-polarized light component, and judges that there exists a contaminant adhering on the surface of the concentration measuring contact, when the calculated value is the same as or more than a given value.

15. The concentration measuring instrument according to claim 14, wherein the judging means judges that there exists no contaminant adhering on the surface of the concentration measuring contact when the value of Ip/Is is in the range of about 0.9 to about 1.1.

16. The concentration measuring instrument according to claim 13, wherein the judging means carries out calculation according to the equation, Is/Ip or $\log_{10}$ (Is/Ip), where Ip represents the measured value of the quantity of the p-polarized light component and Is the measured value of the quantity of the s-polarized light component, and judges that there exists a contaminant adhering on the surface of the concentration measuring contact, when the calculated value is the same as or less than a given value.

17. The concentration measuring instrument according to claim 16, wherein the judging means judges that there exists no contaminant adhering on the surface of the concentration measuring contact when the value of Is/Ip is in the range of about 0.9 to about 1.1.

18. A method of measuring the concentration of a specific component in a subject of measurement utilizing a concentration measuring instrument that has a concentration measuring contact, a light source that emits light and enters the light into the concentration measuring contact and a photodetector, comprising:
a non-contact measuring step of measuring, by the photodetector while keeping the subject of measurement out of contact with the concentration measuring contact, the quantity of light which is emitted and entered by the light source into the concentration measuring contact, passed through or oozed from the concentration measuring contact to the outside thereof and returned to the concentration measuring contact; and a judging step of judging whether a calculation of the concentration of the specific component in the subject of measurement is effective or not by comparing with a threshold a calculated difference obtained by subtracting (2) a reference value, a value, measured by the photodetector while keeping the concentration measuring contact clean, of the quantity of light which is emitted and entered by the light source into the concentration measuring contact, passed through or oozed from the concentration measuring contact to the outside thereof and returned to the concentration measuring contact from (1) a non-contact measured value, a value measured in the non-contact measuring step.

19. A method of measuring the concentration of a specific component in a subject of measurement utilizing a concentration measuring instrument that has a concentration measuring contact, a light source that emits light and enters the light into the concentration measuring contact and a photodetector, comprising:
a non-contact measuring step of measuring by the photodetector the quantity of light which is emitted and entered by the light source into the concentration measuring contact which is once brought into contact with the subject of measurement and then kept out of contact the same, passed though or oozed from the concentration measuring contact to the outside thereof and returned to the concentration measuring contact; and a judging step of judging whether a calculation of the concentration of a specific component in the subject of measurement is effective or not by comparing with a threshold a calculated difference obtained by subtracting (2) a reference value, a value, measured by the photodetector while keeping the concentration measuring contact clean, of the quantity of light which is emitted and entered by the light source into the concentration measuring contact, passed though or oozed from the concentration measuring contact to the outside thereof and returned to the concentration measuring contact from (1) a non-contact measured value, a value measured in the non-contact measuring step.

20. A method of measuring the concentration of a specific component in a subject of measurement, comprising:
a contact measuring step of measuring by photodetector the quantity of light which is emitted and entered by a light source into a concentration measuring contact in contact with the subject of measurement, passed through the concentration measuring contact into the subject of measurement, transmitted in the subject of measurement, and returned to the concentration measuring contact;

a non-contact measuring step of measuring by the photodetector the quantity of light which is emitted and entered by the light source into the concentration measuring contact, which is kept out of contact with the subject of measurement after the contact measuring step, passed through or oozed from the concentration measuring contact to the outside thereof, and returned to the concentration measuring contact; and a calculating step of calculating, after correcting the measured result obtained in the contact measuring step with the measured result obtained in the non-contact measuring step, the concentration of the specific component in the subject of measurement based on the corrected result.

* * * * *

UNITED STATES PATENT AND TRADEMARK OFFICE
CERTIFICATE OF CORRECTION

PATENT NO. : 7,167,735 B2
APPLICATION NO. : 10/480036
DATED : January 23, 2007
INVENTOR(S) : Shinji Uchida et al.

Page 1 of 1

It is certified that error appears in the above-identified patent and that said Letters Patent is hereby corrected as shown below:

Column 18
Line 15, change "incuding" to -- including --

Column 20
Line 25, change "though" to -- through --

Column 20
Line 37, change "though" to -- through --

Column 20
Line 44, after "by" add -- a --

Signed and Sealed this

Nineteenth Day of June, 2007

JON W. DUDAS
*Director of the United States Patent and Trademark Office*